United States Patent [19]

van de Veerdonk

[11] 3,995,630

[45] Dec. 7, 1976

[54] INJECTION SYRINGE WITH TELESCOPIC ASSEMBLY BETWEEN CARTRIDGE AND VIAL

[75] Inventor: Johannes Theodorus Adrianus van de Veerdonk, Eindhoven, Netherlands

[73] Assignee: U.S. Philips Corporation, New York, N.Y.

[22] Filed: Aug. 22, 1975

[21] Appl. No.: 606,969

[30] Foreign Application Priority Data

Sept. 12, 1974 Netherlands ...................... 7412096

[52] U.S. Cl. ........................ 128/218 DA; 128/221; 128/272.1

[51] Int. Cl.[2] ........................................ A61M 5/00

[58] Field of Search ...... 128/218 R, 218 D, 218 M, 128/218 DA, 218 N, 221, 272, 215, 216

[56] References Cited

UNITED STATES PATENTS

| | | | |
|---|---|---|---|
| 3,336,924 | 8/1967 | Sarnoff et al. | 128/218 M |
| 3,375,825 | 4/1968 | Keller | 128/221 |
| 3,826,260 | 7/1974 | Killinger | 128/272 |
| 3,872,867 | 5/1975 | Killinger | 128/272 |

*Primary Examiner*—John D. Yasko
*Attorney, Agent, or Firm*—Frank R. Trifari; David R. Treacy

[57] ABSTRACT

An injection syringe having a cartridge with a hollow injection needle attached thereto; a vial which contains a medicament, closed by a pierceable stopper; and a telescopic assembly which detachably connects the cartridge to the vial. The telescopic assembly consists of two telescopic members, the inner member being detachably connected by an inner and an outer collar to the cartridge, and the outer member being connected to the vial by a snap connection.

3 Claims, 1 Drawing Figure

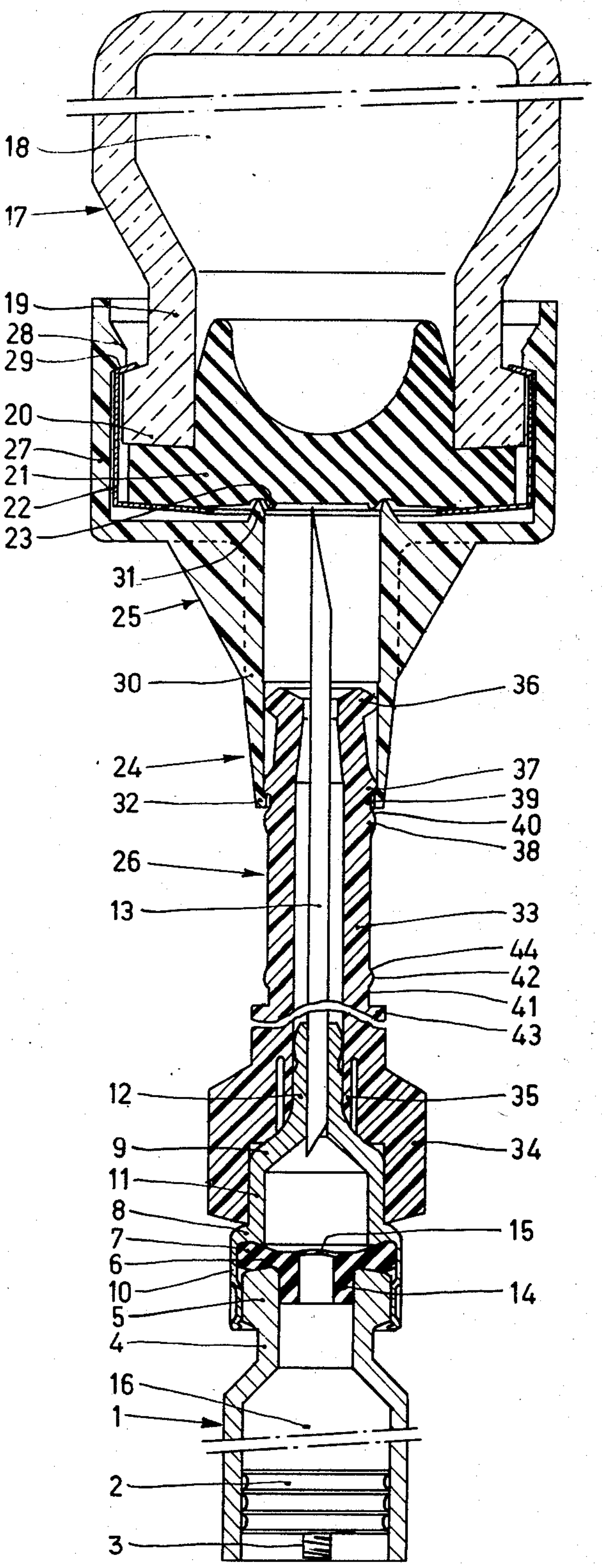
18
17
19
28
29
20
27
21
22
23
31
25
30
36
24
37
32
39
40
38
26
13
33
44
42
41
43
12
35
9
34
11
8
15
7
6
10
14
5
4
16
1
2
3

INJECTION SYRINGE WITH TELESCOPIC ASSEMBLY BETWEEN CARTRIDGE AND VIAL

The invention relates to an injection syringe which consists of a cartridge to which a hollow injection needle is attached, a vial which is closed by a pierceable stopper which constitutes a container for a medicament, and a telescopic assembly which detachably connects the cartridge to the vial.

At one end the cartridge is provided with a plunger which is movable inside the cartridge and at the other end with a needle mount which at the cartridge end comprises a substantially cylindrical wall portion and at the other end is provided with a cylindrical sleeve in which the injection needle is secured.

The telescopic assembly comprises an outer telescopic member which is connected to the vial and an inner telescopic member of which one end is detachably connected to the cartridge and whose other end extends into the outer telescopic member.

The injection needle is disposed in a central bore of the inner telescopic member and extends beyond the end of said member.

Such an injection syringe is known from the Applicant's British Patent Specification No. 1,043,954. FIGS. 6 and 7 of said Specification and the description reveal that the inner telescopic member is clamped on the cylindrical sleeve via the central bore. The connection between cartridge and vial which is based on said clamping fit, is not very rigid in particular when heavy vials are employed, and may for example during transport readily give rise to deformations and damaging of the injection syringe. Moreover, because of the necessary rigidity of the telescopic member, the sealing of member and sleeve with respect to bacterial contamination is not optimum. Another drawback is that for example during transport the vial and cartridge are moved relative to each other owing to a telescoping movement of the telescopic assembly, so that vial and cartridge are removed from each other or, alternatively, the injection needle pierces the rubber stopper of the vial so that the contents of the cartridge can prematurely come into contact with the contents of the vial.

The Applicant has now developed an injection syringe of the type mentioned in the preamble which does not have said drawbacks. The injection syringe according to the invention is characterized in that the inner telescopic member at the cartridge end is provided with an outer collar of comparatively great wall thickness whose inner surface frictionally engages with the outer surface of the cylindrical portion of the needle mount, and with an inner collar of comparatively small wall thickness whose inner surface engages with the outer wall of the cylindrical sleeve.

Due to the use of the outer collar a rigid, shock-proof connection is obtained between cartridge and vial, while the flexible inner collar provides satisfactory sealing with respect to bacteria and other micro-organisms, even in the event of great tolerance differences of the dimensions of the relevant components.

In a suitable embodiment the inner telescopic member near the end which is remote from the cartridge is provided with a groove, which groove in co-operation with a cam which is provided at the outer telescopic member constitutes a locking of the inner and the outer telescopic member, the wall portion of the groove and/or the cam which faces the cartridge having a conical shape.

In a further suitable embodiment the inner telescopic member is provided with two closely spaced ridges between which the groove is formed.

The locking provided by the groove and cam can be released owing to the conical shape of the wall portion of the groove and/or cam which is located at the side of the cartridge, by exerting a sufficiently great inwardly directed force on the vial and/or the cartridge. The required force is greater than the forces exerted on the injection syringe during transportation.

The invention will be described in more detail with reference to the accompanying drawing.

The FIGURE shows a cross-section of the injection syringe according to the invention.

In the FIGURE the reference numeral 1 denotes a cartridge which at one end contains a plunger 2 which is movable therein and which is provided with a coupling member 3 for a plunger rod. The plunger rod is not shown. At the other end the cartridge 1 is provided with a neck 4 with flange portion 5. The cartridge 1 is closed by a rubber stopper 6, the flange portion 7 of stopper 6 being clamped between flange portion 5 of cartridge 1 and a flange 8 of needle mount 9. Clamping is effected by means of a collar 10 of needle mount 9 which is bent around flange portion 5 and flange portion 7.

Near the stopper 6 needle mount 9 is provided with a substantially cylindrical wall portion 11. At the other end needle mount 9 is provided with a substantially cylindrical sleeve 12 in which a hollow injection needle 13 which is pointed at both ends is secured. In addition to the said flange portion 7 the stopper 6 also comprises a cylindrical portion 14 with a central duct which at the top is closed by a diaphragm 15. Between stopper 6 and plunger 2 the cartridge 1 contains a liquid medium 16 such as for example distilled water, a physiological salt solution or a liquid medicament.

The reference numeral 17 denotes a vial which constitutes a container for a medicament 18 which is for example present in dry form. The vial 18 comprises a neck portion 19 and adjoining said portion a flange 20. Vial 18 is closed by a rubber stopper 21, a metal capsule 22 with a circular opening being crimped around the rubber stopper 21 and underneath flange 20. The rubber stopper 21 is provided with a ridge 23 at its top.

Cartridge 1 and vial 18 are mutually connected by a telescopic assembly which is denoted by the general reference numeral 24. Assembly 24 consists of an outer telescopic member 25 and an inner telescopic member 26. Member 25 comprises a jacket 27 which is snapped around capsule 22 and which for this purpose is provided with an edge 28 with a conical surface 29. The member 25 further comprises a guide element 30 and a circular edge 31 which penetrates the rubber stopper 21. The guide element 30 is provided with a cam 32 at the end which is remote from the jacket 27. The member 26 comprises a cylindrical body 33 which at one end is provided with an outer collar 34 with a comparatively great wall thickness and which with the inner surface is clamped onto cylindrical wall portion 11 of needle mount 9. The end of member 26 which faces collar 34 is furthermore provided with an inner collar 35 whose wall thickness is relatively small. As a result of the small wall thickness but also owing to the choice of the material, such as plastic, the inner collar 35 is flexible. This provides a satisfactory sealing between collar 35 and sleeve 12. The end of body 33 which faces away from the inner and the outer collar has a conical shape and is provided with a guide ridge 36 which with the outer edge engages with the inner surface of guide element 30. Near said end body 33 is provided with two ridges 37, 38 between which a groove 39 is formed. The side wall 40 of ridge 38 has a conical shape. Cam 32 of the outer telescopic member 24 engages with groove 39. At some distance from ridges 37, 38 the cylindrical body 33 is provided with a second groove 41 which is disposed between a ridge 42 and a thickened wall portion 43. Wall portion 44 of ridge 42 is conically shaped.

When the injection syringe according to the invention is used cartridge 1 and vial 17 are moved towards each other. Owing to the force which is exerted, cam 32 is released from groove 39 via the conical surface 40 of rib 38. As a result of this the outer telescopic member 26 is moved in the inner telescopic member 25, the guide ridge 36 of member 26 sliding along the inner surface of guide element 30. During this movement needle 13 penetrates the rubber stopper 21. The movement of cartridge and vial towards each other continues until cam 32 touches the thickened wall portion 43 of the member 26. In this extreme position cam 32 engages with groove 41. Needle 13 then has fully pierced stopper 21 of vial 17 with the bevelled end. Subsequently a force is exerted on the liquid 16 contained in the cartridge 1 via plunger 2. As a result the diaphragm 15 bulges up until it is ruptured either spontaneously or upon contact with the sharp rear tip of needle 13. Upon further pressure on plunger 2 it moves inside cartridge 1 and the liquid 16 contained in the cartridge is injected into the vial 17 via needle 13. The contents of vial 17 is dissolved or suspended in the liquid 16, after which the resulting substance is sucked into cartridge 1 by withdrawing the plunger 2 completely. This suction is optimum if the injection syringe is held in a vertical position, the vial 17 being disposed above cartridge 1. Subsequently an opposite outwardly directed force is exerted on vial 17 and cartridge 1. As the frictional force between collars 34, 35 and needle mount 9 is smaller than the force which is required to release cam 32 from groove 41, the cartridge 1 with needle mount 9 and needle 13 will be released from the inner telescopic member 26 and will eventually be entirely clear of vial 17 with the outer telescopic member 25 and inner telescopic member 26 connected thereto. The cartridge 1 is now ready for giving an injection.

What is claimed is:

1. An injection syringe which comprises a cartridge to which an injection needle is attached, a vial which is closed by a pierceable stopper which constitutes a container for a medicament, and a telescopic assembly which detachably connects the cartridge and the vial, in which the cartridge at one end is provided with a plunger which is movable inside the cartridge and at the other end with a needle mount which at the cartridge end comprises a substantially cylindrical wall portion and at the other end is provided with a sleeve in which the injection needle is secured and in which the telescopic assembly comprises an outer telescopic member which is connected to the vial and an inner telescopic member of which one end is detachably connected to the cartridge and whose other end extends into the outer telescopic member, the injection needle furthermore extending through a central bore in the inner telescopic member beyond its end, characterized in that the inner telescopic member at the side of the cartridge is provided with an outer collar of relatively great wall thickness whose inner surface frictionally engages with the outer surface of the cylindrical portion of the needle mount and with an inner collar of relatively small wall thickness whose inner surface engages with the outer wall of the cylindrical sleeve.

2. An injection syringe as claimed in claim 1, characterized in that the inner telescopic member near the end which is remote from the cartridge is provided with a groove which in co-operation with a cam which is provided at the outer telescopic member constitutes a locking of the inner and the outer telescopic member, the wall portion of he groove and/or cam which faces the cartridge having a conical shape.

3. An injection syringe as claimed in claim 1, characterized in that the inner telescopic member is provided with two closely spaced ridges between which the groove is formed.

* * * * *